(12) United States Patent
Simon et al.

(10) Patent No.: US 12,201,850 B2
(45) Date of Patent: Jan. 21, 2025

(54) HIGH DOSE RATE RADIATION THERAPY SYSTEMS AND DOSIMETRY

(71) Applicant: Sun Nuclear Corporation, Melbourne, FL (US)

(72) Inventors: William E. Simon, Satellite Beach, FL (US); Jakub Kozelka, Melbourne, FL (US); Jeffrey L. Hildreth, Melbourne, FL (US); Andreas A. Schönfeld, Wendeburg (DE); Myron Brookshire, Melbourne, FL (US)

(73) Assignee: Sun Nuclear Corporation, Melbourne, FL (US)

( * ) Notice: Subject to any disclaimer, the term of this patent is extended or adjusted under 35 U.S.C. 154(b) by 142 days.

(21) Appl. No.: 17/842,674

(22) Filed: Jun. 16, 2022

(65) Prior Publication Data

US 2023/0405357 A1 Dec. 21, 2023

(51) Int. Cl.
*A61N 5/10* (2006.01)
*G01T 1/24* (2006.01)

(52) U.S. Cl.
CPC ......... *A61N 5/1031* (2013.01); *A61N 5/1048* (2013.01); *A61N 5/1071* (2013.01); *A61N 5/1075* (2013.01); *G01T 1/247* (2013.01); *A61N 2005/1074* (2013.01)

(58) Field of Classification Search
CPC .. A61N 5/1031; A61N 5/1048; A61N 5/1071; A61N 5/1075; A61N 2005/1074
See application file for complete search history.

(56) References Cited

U.S. PATENT DOCUMENTS

| | | | |
|---|---|---|---|
| 759,608 | A | 5/1904 | Harper |
| 1,239,145 | A | 9/1917 | Wantz |
| 2,818,510 | A | 12/1957 | Verse |
| 3,033,985 | A | 5/1962 | Petree |
| 3,267,728 | A | 8/1966 | Solomons |

(Continued)

FOREIGN PATENT DOCUMENTS

| | | |
|---|---|---|
| CA | 2718408 | 9/2009 |
| DE | 102009039345 A1 | 3/2011 |

(Continued)

OTHER PUBLICATIONS

Jaccard, Maud, et al. "High dose-per-pulse electron beam dosimetry: commissioning of the Oriatron eRT6 prototype linear accelerator for preclinical use." Medical physics 45.2 (2018): 863-874. (Year: 2018).*

(Continued)

*Primary Examiner* — Sean D Mattson

(74) *Attorney, Agent, or Firm* — Pillsbury Winthrop Shaw Pittman LLP

(57) ABSTRACT

Disclosed is a system for quality assurance of high dose rate radiation therapy. The system includes a radiation delivery system configured to deliver high dose rate radiation therapy, with the radiation delivery system including a radiation source and a collimating system. The system also includes a radiation detection system having a diode to measure high dose rate radiation from the radiation source, an operational amplifier to transform the output of the diode to a measurable voltage, and a voltage source configured to apply a reverse bias to a component of the radiation detection system.

11 Claims, 7 Drawing Sheets

(56) References Cited

U.S. PATENT DOCUMENTS

| | | | |
|---|---|---|---|
| 3,327,213 | A | 6/1967 | Wald, Jr. |
| 3,394,258 | A | 7/1968 | Schleiger |
| 3,433,953 | A | 3/1969 | Sweet |
| 3,665,762 | A | 5/1972 | Domen |
| 3,783,251 | A | 1/1974 | Pavkovich |
| 3,790,794 | A | 2/1974 | Murray |
| 3,978,336 | A | 8/1976 | Roux |
| 3,980,885 | A | 9/1976 | Steward |
| 4,058,832 | A | 11/1977 | Vagi |
| 4,063,097 | A | 12/1977 | Barrett |
| 4,107,531 | A | 8/1978 | Garratt |
| 4,157,472 | A | 6/1979 | Barrett |
| 4,312,224 | A | 1/1982 | Domen |
| 4,450,440 | A | 5/1984 | White |
| 4,455,609 | A | 6/1984 | Inamura |
| 4,613,754 | A | 9/1986 | Vinegar |
| 4,729,099 | A | 3/1988 | Iverson |
| 4,765,749 | A | 8/1988 | Bourgade |
| 4,777,442 | A | 10/1988 | Rosenthal |
| 4,871,914 | A * | 10/1989 | Simon ............... G01T 1/247 250/DIG. 2 |
| 4,887,287 | A | 12/1989 | Cobben |
| 5,059,801 | A * | 10/1991 | Burgess ............... G01T 1/026 250/370.07 |
| 5,099,505 | A | 3/1992 | Seppi |
| 5,160,337 | A | 11/1992 | Cosman |
| 5,262,649 | A | 11/1993 | Antonuk |
| 5,388,142 | A | 2/1995 | Morris |
| 5,394,452 | A | 2/1995 | Swerdloff |
| 5,596,653 | A | 1/1997 | Kurokawa |
| 5,602,892 | A | 2/1997 | Llacer |
| 5,621,214 | A | 4/1997 | Sofield |
| 5,622,187 | A | 4/1997 | Carol |
| 5,627,367 | A | 5/1997 | Sofield |
| 5,635,709 | A | 6/1997 | Sliski |
| 5,640,436 | A | 6/1997 | Kawai |
| 5,652,430 | A * | 7/1997 | Lee ............... G01T 1/247 250/578.1 |
| 5,661,310 | A | 8/1997 | Jones |
| 5,704,890 | A | 1/1998 | Bliss |
| 5,712,482 | A | 1/1998 | Gaiser |
| 5,873,826 | A | 2/1999 | Gono |
| 5,988,875 | A | 11/1999 | Gershfeld |
| 6,038,283 | A | 3/2000 | Carol |
| 6,125,335 | A | 9/2000 | Simon |
| 6,131,690 | A | 10/2000 | Galando |
| 6,148,272 | A | 11/2000 | Bergstrom |
| 6,175,761 | B1 | 1/2001 | Frandsen |
| 6,207,952 | B1 | 3/2001 | Kan |
| 6,257,552 | B1 | 7/2001 | Crow |
| 6,261,219 | B1 | 7/2001 | Meloul |
| 6,301,329 | B1 | 10/2001 | Surridge |
| 6,322,249 | B1 | 11/2001 | Wofford |
| 6,345,114 | B1 | 2/2002 | Mackie |
| 6,364,529 | B1 | 4/2002 | Dawson |
| 6,398,710 | B1 | 6/2002 | Ishikawa |
| 6,466,644 | B1 * | 10/2002 | Hughes ............... A61N 5/1048 378/65 |
| 6,516,046 | B1 | 2/2003 | Stephan |
| 6,535,574 | B1 | 3/2003 | Collins |
| 6,535,756 | B1 | 3/2003 | Simon |
| 6,552,347 | B1 | 4/2003 | Dimcovski |
| 6,560,311 | B1 | 5/2003 | Shepard |
| 6,594,336 | B2 | 7/2003 | Nishizawa |
| 6,609,626 | B2 | 8/2003 | Young |
| 6,609,826 | B1 | 8/2003 | Fujii |
| 6,626,569 | B2 | 9/2003 | Reinstein |
| 6,636,622 | B2 | 10/2003 | Mackie |
| 6,648,503 | B2 | 11/2003 | Tanaka |
| 6,712,508 | B2 | 3/2004 | Nilsson |
| 6,788,759 | B2 | 9/2004 | Op De Beek |
| 6,799,068 | B1 | 9/2004 | Hartmann |
| 6,810,107 | B2 | 10/2004 | Steinberg |
| 6,810,108 | B2 | 10/2004 | Clark |
| 6,833,707 | B1 | 12/2004 | Dahn |
| 6,839,404 | B2 | 1/2005 | Clark |
| 6,853,702 | B2 | 2/2005 | Renner |
| 6,888,919 | B2 | 5/2005 | Graf |
| 6,904,119 | B2 | 6/2005 | Oikawa |
| 6,904,125 | B2 | 6/2005 | Van Dyk |
| 6,904,162 | B2 | 6/2005 | Robar |
| 6,974,254 | B2 | 12/2005 | Paliwal |
| 6,990,368 | B2 | 1/2006 | Simon |
| 6,992,309 | B1 | 1/2006 | Petry |
| 7,016,454 | B2 | 3/2006 | Warnberg |
| 7,065,812 | B2 | 6/2006 | Newkirk |
| 7,076,023 | B2 | 7/2006 | Ghelmansarai |
| 7,098,463 | B2 | 8/2006 | Adamovics |
| 7,116,749 | B2 | 10/2006 | Besson |
| 7,125,163 | B2 | 10/2006 | Eigler |
| 7,127,028 | B2 | 10/2006 | Sendai |
| 7,127,030 | B2 | 10/2006 | Tamegai |
| 7,142,634 | B2 | 11/2006 | Engler |
| 7,193,220 | B1 | 3/2007 | Navarro |
| 7,221,733 | B1 | 5/2007 | Takai |
| 7,233,688 | B2 | 6/2007 | Ritt |
| 7,234,355 | B2 | 6/2007 | Dewangan |
| 7,298,820 | B2 | 11/2007 | Nelson |
| 7,339,159 | B2 | 3/2008 | Juh |
| 7,349,523 | B2 | 3/2008 | Jenkins |
| 7,352,840 | B1 | 4/2008 | Nagarkar |
| 7,371,007 | B2 | 5/2008 | Nilsson |
| 7,386,089 | B2 | 6/2008 | Endo |
| 7,420,160 | B2 | 9/2008 | Delaperriere |
| 7,453,976 | B1 | 11/2008 | Yin |
| 7,455,449 | B2 | 11/2008 | Nishimura |
| 7,471,765 | B2 | 12/2008 | Jaffray |
| 7,515,681 | B2 | 4/2009 | Ebstein |
| 7,579,608 | B2 | 8/2009 | Takahashi |
| 7,605,365 | B2 | 10/2009 | Chen |
| 7,636,419 | B1 | 12/2009 | Nelson |
| 7,668,292 | B1 | 2/2010 | Bose |
| 7,734,010 | B2 | 6/2010 | Otto |
| 7,750,311 | B2 | 7/2010 | Daghighian |
| 7,766,903 | B2 | 8/2010 | Blumenkranz |
| 7,773,723 | B2 | 8/2010 | Nord |
| 7,778,383 | B2 | 8/2010 | Koehler |
| 7,778,392 | B1 | 8/2010 | Berman |
| 7,778,680 | B2 | 8/2010 | Goode, Jr. |
| 7,782,998 | B2 | 8/2010 | Langan |
| 7,945,022 | B2 | 5/2011 | Nelms |
| 8,044,359 | B2 | 10/2011 | Simon |
| 8,093,549 | B2 | 1/2012 | Navarro |
| 8,130,905 | B1 | 3/2012 | Nelms |
| 8,136,773 | B2 | 3/2012 | Schmutzer |
| 8,147,139 | B2 | 4/2012 | Papaioannou |
| 8,218,718 | B1 | 7/2012 | Van Herk |
| 8,235,530 | B2 | 8/2012 | Maad |
| 8,242,458 | B2 | 8/2012 | Rinecker |
| 8,321,179 | B2 | 11/2012 | Simon |
| 8,325,878 | B2 | 12/2012 | McNutt |
| 8,430,564 | B2 | 4/2013 | Simmons |
| 8,457,713 | B2 | 6/2013 | Kagermeier |
| 8,474,794 | B2 | 7/2013 | Liljedahl |
| 8,536,547 | B2 | 9/2013 | Maurer |
| 8,541,756 | B1 | 9/2013 | Treas |
| 8,605,857 | B1 | 12/2013 | Renner |
| 8,632,448 | B1 | 1/2014 | Schulte |
| 8,726,814 | B1 | 5/2014 | Matteo |
| 8,794,899 | B2 | 8/2014 | Cozza |
| 8,833,709 | B2 | 9/2014 | Weng |
| 8,840,304 | B2 | 9/2014 | Perez Zarate |
| 8,840,340 | B2 | 9/2014 | Eisenhower |
| 8,874,385 | B2 | 10/2014 | Takayanagi |
| 8,927,921 | B1 | 1/2015 | Nelms |
| 9,050,460 | B2 | 6/2015 | Hildreth |
| 9,097,384 | B1 | 8/2015 | Simon |
| 9,310,263 | B2 | 4/2016 | Thoen |
| 9,463,336 | B2 | 10/2016 | Nelms |
| 9,480,861 | B2 | 11/2016 | Kapatoes |
| 9,561,388 | B2 | 2/2017 | Hildreth |
| 9,586,060 | B2 | 3/2017 | Seuntjens |
| 9,750,955 | B2 | 9/2017 | McNutt |
| 9,895,557 | B2 | 2/2018 | Seuntjens |

(56) References Cited

U.S. PATENT DOCUMENTS

| | | |
|---|---|---|
| 10,099,067 B2 | 10/2018 | Kapatoes |
| 10,413,754 B2 | 9/2019 | Seuntjens |
| 10,755,823 B2 | 8/2020 | Carette |
| 2001/0042841 A1 | 11/2001 | Lyons |
| 2002/0077545 A1 | 6/2002 | Takahashi |
| 2002/0080912 A1 | 6/2002 | Mackie |
| 2003/0043879 A1 | 3/2003 | Tanaka |
| 2003/0043960 A1 | 3/2003 | Op De Beek |
| 2003/0138077 A1 | 7/2003 | Lee |
| 2003/0231740 A1 | 12/2003 | Paliwal |
| 2004/0066880 A1 | 4/2004 | Oikawa |
| 2004/0068182 A1 | 4/2004 | Misra |
| 2004/0096033 A1 | 5/2004 | Seppi |
| 2004/0113094 A1 | 6/2004 | Lyons |
| 2004/0120560 A1 | 6/2004 | Robar |
| 2004/0129888 A1* | 7/2004 | Kannan ............ G01T 1/026 250/370.07 |
| 2004/0158145 A1 | 8/2004 | Ghelmansarai |
| 2004/0211917 A1 | 10/2004 | Adamovics |
| 2004/0228435 A1 | 11/2004 | Russell |
| 2004/0251419 A1 | 12/2004 | Nelson |
| 2005/0013406 A1 | 1/2005 | Dyk |
| 2005/0077459 A1 | 4/2005 | Engler |
| 2005/0111621 A1 | 5/2005 | Riker |
| 2005/0281389 A1 | 12/2005 | Kusch |
| 2006/0002519 A1 | 1/2006 | Jenkins |
| 2006/0033044 A1 | 2/2006 | Gentry |
| 2006/0184124 A1 | 8/2006 | Cowan |
| 2006/0203964 A1 | 9/2006 | Nyholm |
| 2006/0203967 A1 | 9/2006 | Nilsson |
| 2006/0266951 A1 | 11/2006 | Fritsch |
| 2007/0041497 A1 | 2/2007 | Schnarr |
| 2007/0041499 A1 | 2/2007 | Lu |
| 2007/0053492 A1 | 3/2007 | Kidani |
| 2007/0071169 A1 | 3/2007 | Yeo |
| 2007/0081629 A1 | 4/2007 | Yin |
| 2007/0086577 A1 | 4/2007 | Kobayashi |
| 2007/0172020 A1 | 7/2007 | Nambu |
| 2007/0181815 A1 | 8/2007 | Ebstein |
| 2007/0195930 A1 | 8/2007 | Kapatoes |
| 2008/0031406 A1 | 2/2008 | Yan |
| 2008/0049896 A1 | 2/2008 | Kuduvalli |
| 2008/0049898 A1 | 2/2008 | Romesberg, III |
| 2008/0091388 A1 | 4/2008 | Failla |
| 2008/0103834 A1 | 5/2008 | Reiner |
| 2008/0118137 A1 | 5/2008 | Chen |
| 2008/0260368 A1 | 10/2008 | Chang |
| 2008/0292055 A1 | 11/2008 | Boone |
| 2008/0298553 A1 | 12/2008 | Takahashi |
| 2009/0003512 A1 | 1/2009 | Pouliot |
| 2009/0003528 A1 | 1/2009 | Ramraj |
| 2009/0067576 A1 | 3/2009 | Maltz |
| 2009/0090870 A1 | 4/2009 | Ahnesjo |
| 2009/0175418 A1 | 7/2009 | Sakurai |
| 2009/0217999 A1 | 9/2009 | Becker |
| 2009/0227841 A1 | 9/2009 | Miyako |
| 2009/0250618 A1 | 10/2009 | Simon |
| 2009/0252292 A1 | 10/2009 | Simon |
| 2009/0326365 A1 | 12/2009 | Goldenberg |
| 2010/0008467 A1 | 1/2010 | Dussault |
| 2011/0022360 A1 | 1/2011 | Simon |
| 2011/0051893 A1 | 3/2011 | McNutt |
| 2011/0085716 A1 | 4/2011 | Chefd Hotel |
| 2011/0096906 A1 | 4/2011 | Langeveld |
| 2011/0108702 A1* | 5/2011 | Jackson ............ G01T 1/248 250/207 |
| 2011/0158386 A1 | 6/2011 | Payne |
| 2011/0204262 A1 | 8/2011 | Pu |
| 2011/0210258 A1 | 9/2011 | Black |
| 2011/0248188 A1 | 10/2011 | Brusasco |
| 2011/0278444 A1 | 11/2011 | Navarro |
| 2011/0306864 A1 | 12/2011 | Zarate |
| 2012/0014618 A1 | 1/2012 | Sun |
| 2012/0025105 A1 | 2/2012 | Brown |
| 2012/0025826 A1 | 2/2012 | Zhou |
| 2012/0097860 A1* | 4/2012 | Oguma ............ A61B 6/4283 250/394 |
| 2012/0230462 A1 | 9/2012 | Robar |
| 2012/0292517 A1 | 11/2012 | Izaguirre |
| 2012/0305793 A1 | 12/2012 | Schiefer |
| 2012/0326057 A1 | 12/2012 | Remeijer |
| 2013/0048869 A1 | 2/2013 | Kominami |
| 2013/0048883 A1 | 2/2013 | Simon |
| 2013/0258105 A1 | 10/2013 | Jozsef |
| 2013/0287170 A1 | 10/2013 | Ebstein |
| 2013/0303902 A1 | 11/2013 | Smith |
| 2014/0016754 A1 | 1/2014 | Sugiyama |
| 2014/0064445 A1 | 3/2014 | Adler |
| 2014/0073834 A1 | 3/2014 | Hildreth |
| 2014/0077098 A1 | 3/2014 | Tachikawa |
| 2014/0094642 A1 | 4/2014 | Fuji |
| 2014/0105355 A1 | 4/2014 | Toimela |
| 2014/0221816 A1 | 8/2014 | Franke |
| 2014/0237213 A1 | 8/2014 | Gill |
| 2014/0250480 A1 | 9/2014 | Koh |
| 2014/0263990 A1 | 9/2014 | Kawrykow |
| 2015/0071408 A1 | 3/2015 | Ebstein |
| 2015/0080634 A1 | 3/2015 | Huber |
| 2015/0087879 A1 | 3/2015 | Nelms |
| 2015/0108356 A1 | 4/2015 | Seuntjens |
| 2015/0124930 A1 | 5/2015 | Verhaegen |
| 2015/0238778 A1 | 8/2015 | Hildreth |
| 2015/0283403 A1 | 10/2015 | Kapatoes |
| 2015/0309193 A1 | 10/2015 | Kozelka |
| 2015/0327825 A1 | 11/2015 | Suzuki |
| 2015/0352376 A1 | 12/2015 | Wiggers |
| 2016/0067479 A1 | 3/2016 | Marcovecchio |
| 2016/0136460 A1 | 5/2016 | Baltes |
| 2016/0166857 A1 | 6/2016 | Nelms |
| 2016/0256712 A1 | 9/2016 | Vahala |
| 2016/0287906 A1 | 10/2016 | Nord |
| 2016/0310762 A1 | 10/2016 | Ramezanzadeh Moghadam |
| 2016/0361568 A1 | 12/2016 | Chappelow |
| 2017/0021194 A1 | 1/2017 | Nelms |
| 2017/0135580 A1 | 5/2017 | Lips |
| 2017/0173367 A1 | 6/2017 | Seuntjens |
| 2017/0177812 A1 | 6/2017 | Sjölund |
| 2017/0225015 A1 | 8/2017 | Thieme |
| 2017/0274225 A1 | 9/2017 | Baecklund |
| 2018/0014798 A1 | 1/2018 | Beckman |
| 2018/0028143 A1 | 2/2018 | Wiggers |
| 2018/0028840 A1 | 2/2018 | Simon |
| 2018/0043183 A1 | 2/2018 | Sheng |
| 2018/0140272 A1 | 5/2018 | Ruchala |
| 2018/0185672 A1 | 7/2018 | Ramezanzadeh Moghadam |
| 2018/0243586 A1 | 8/2018 | Ramezanzadeh Moghadam |
| 2018/0250529 A1 | 9/2018 | Seuntjens |
| 2018/0250531 A1 | 9/2018 | Ansorge |
| 2019/0014243 A1 | 1/2019 | Malone |
| 2019/0118002 A1 | 4/2019 | Rosenwald |
| 2019/0298285 A1 | 10/2019 | Rakic |
| 2020/0101327 A1 | 4/2020 | Alquist |
| 2020/0253001 A1 | 8/2020 | Nauditt |
| 2021/0011178 A1 | 1/2021 | Kapatoes |
| 2021/0012507 A1 | 1/2021 | Kapatoes |
| 2021/0015441 A1 | 1/2021 | Bourne |
| 2021/0220676 A1 | 7/2021 | Kawrykow |
| 2021/0236856 A1 | 8/2021 | Kapatoes |

FOREIGN PATENT DOCUMENTS

| | | | |
|---|---|---|---|
| EP | 1060726 | 12/2000 | |
| EP | 1060726 B1 | 6/2004 | |
| EP | 2016445 | 1/2009 | |
| EP | 2078537 A1 | 7/2009 | |
| EP | 2117649 A2 | 11/2009 | |
| EP | 2186542 | 5/2010 | |
| EP | 2400317 A1 * | 12/2011 | ............ G01T 1/026 |
| EP | 2457237 | 5/2012 | |
| EP | 2708919 A2 | 3/2014 | |
| EP | 2865417 | 4/2015 | |
| EP | 2904974 | 8/2015 | |
| EP | 3074088 | 10/2016 | |
| EP | 3075417 | 10/2016 | |

(56) References Cited

FOREIGN PATENT DOCUMENTS

| | | |
|---|---|---|
| JP | 05154209 | 6/1993 |
| JP | 2003310590 A | 11/2003 |
| JP | 2008105882 | 5/2008 |
| JP | 2010215428 | 9/2010 |
| JP | 2010234521 | 10/2010 |
| JP | 202035449 | 3/2020 |
| WO | 2006138513 | 12/2006 |
| WO | 2008013956 | 1/2008 |
| WO | 2009114669 | 9/2009 |
| WO | 2009120494 | 10/2009 |
| WO | 2009137794 | 11/2009 |
| WO | 2011011471 | 1/2011 |
| WO | 2012053440 | 4/2012 |
| WO | 2013049839 | 4/2013 |
| WO | 2013177677 A | 12/2013 |
| WO | 2015024360 | 2/2015 |
| WO | 2015073899 | 5/2015 |
| WO | 2016172352 | 10/2016 |
| WO | 2016200463 | 12/2016 |
| WO | 2019157249 A | 8/2019 |

OTHER PUBLICATIONS

Barthe, Jean. "Electronic dosimeters based on solid state detectors." Nuclear Instruments and Methods in Physics Research Section B: Beam Interactions with Materials and Atoms 184.1-2 (2001): 158-189. (Year: 2001).*

Albers et al., CRC HAndbook of Chemistry and Physics, 87th Ed., Edited by R.C. Weast CRC, Cleveland, 1976. pp. F-11, D-171, E-6. (4 pages).

Almond et al. In "AAPM TG-51 Protocol for Clinical Reference Dosimetry of High Energy Photon and Electron Beams", Med. Phys. VI, 26, pp. 1847-1870, 1999.

Aspen Aerogels, Pyrogel.RTM. 2250 Datasheet (Aspen Aerogels, Inc., Northborough, 2010). 2 pages.

Berlyand et al., "Portable Calorimeter for Measuring Absorbed Doses of X-Rays and Electrons from Accelerators", translated from Izeritel'naya Teknika, No. 11, Nov. 1991, pp. 56-58.

Boutillon in "Gap Correction for the Calorimetric Measurement of Absorbed Dose in Graphite with a 60Co Beam", Phys. Med. Biol., vol. 34, pp. 1809-1821, 1989.

Daures et al., "New Constant-Temperature Operating Mode for Graphite Calorimeter at LNE-LNHB", Physics in Medicine and Biology, vol. 50, 2005, No. pp. 4035-4052.

Daures et al., "Small section graphite calorimeter (CR10) at LNE-LNHB for measurement in small beams for IMRT", Metrologica, (Dec. 1, 2011), XP020229547, 5 pages.

Daures et al., "Small Section Graphite Calorimeter (GR-10) at LNE-LNHB for Measurements in Small Beams for IMRT Metrologia", vol. 49, No. 5, 2012, pp. S174-S178.

Domen et al., "A Heat-loss-Compensated Calori meter: Theory, Design, and Performance", Journal of Research of the National Bureau of Standards—A. Physics and Chemistry, vol. 78A, No. 5, Sep.-Oct. 1974, pp. 595-610.

Domen, "Absorbed Dose Water Calorimeter", (Med. Phys., vol. 7, 1980, pp. 157-159).

Duane et al., "An Absorbed Dose Calorimeter for IMRT Dosimetry", Metrologia, vol. 49, No. 5, 2012, pp. S168-S173.

Iaea, Trs., "398. Absorbed Dose Determination in External Beam Radiotherapy: An International Code of Practice for Dosimetry based on Standards of Absorbed Dose to Water," Vienna International Atomic Energy Agency (2000). 242 pages.

J. Seuntjens and S. Duane, "Photon absorbed dose standards," Metrologia 46, S39-S58 (2009).

Kawrakow et al. In "The EGSnrc Code System: Monte-Carlo Simulation of Electron and Photon Transport" (Canadian National Research Center, NRC Report PIRS-701, 2006.

McEwen at al., 'A Portable Calorimeter for Measuring Absorbed Dose in the Radiotherapy Clinic', Physics in Medicine and Biology, vol. 45, No. 12, Dec. 2000, pp. 3675-3691.

McDonald et al., "Portable Tissue Equivalent Calorimeter", Medical Physics, vol. 3, 2, Mar.-Apr. 1976, pp. 80-86.

McEwen et al., "Portable Graphite Calorimeter for Measuring Absorbed Dose in the Radiotherapy Clinic", Standards and Codes of Practice in Medical Radiation Dosimetry, IAEA-CN-96-9P,2002, pp. 115-121.

Miller, "Polystyrene Calorimeter for Electron Beam Dose Measurements", Radiation Physics Chemistry vol. 46, No. 4-6, Aug. 1995, pp. 1243-1246.

Myers et al., "Precision Adiabatic Gamma-Ray Calorimeter using Thermistor Thermometry", Review of Scientific Instruments, vol. 32, No. 9, Sep. 1961, pp. 1013-1015.

Nutbrown et. "Evaluation of Factors to Convert Absorbed Dose Calibrations in Graphite to Water for Mega-Voltage Photon Beams" (UK National Pysical Laboratory, NPL Report CIRM 37, 2000. 45 pages.

Ostrowsky et al., "The Construction of the Graphite Calorimeter GR9 at LNE-LNHB (Geometrical and technical considerations)", Report CEA-R-6184, 2008, 52 pages.

Owen et al "Correction for the Effect of the Gaps around the Core of an Absorbed Dose Graphite Calorimeter in High Energy Photon Radiation" (Phys. Med. Biol., vol. 36, pp. 1699-1704, 1991.

Palmans et al., "A Small-Body Portable Graphite Calorimeter for Dosimetry in Low-Energy Clinical Proton Beams", Physics in Medicine and Biology, vol. 49, No. 16, Aug. 2004, pp. 3737-3749.

Petree et al., "A Comparison of Absorbed Dose Determinations in Graphite by Cavity Ionization Measurements and by Calorimetry", Journal of Research of the National Bureau of Standards—C. Engineering and Instrumentation. vol. 71 C, No. 1, Jan.-Mar. 1967, pp. 19-27.

Picard et al., "Construction of an Absorbed-Dose Graphite Calorimeter", Report BIPM-09/01' May 2009, 12 pages.

R. Alfonso et al., 'A new formalism for reference dosimetry of small and nonstandard fields,' Med. Phys. 35, 5179-5186 (2008).

Renaud et al., "Development of a graphite probe calorimeter for absolute clinical dosimetry", Med. Phvs., (Jan. 9, 2013), vol. 40, No. 2, p. 020701, XP012170941, 6 pages.

Rogers, "The physics of AAPM's TG-51 protocol," in Clinical Dosimetry Measurements in Radiotherapy, Medical Physics Monograph No. 34, edited by D. W. O. Rogers and J. E. Cygler (Medical Physics Publishing, Madison, WI, 2009), pp. 239-298.

Ross et al. In "Water Calorimetry for Radiation Dosimetry" (Phys. Med. Biol., 1996, vol. 41, pp. 1-29).

S. Picard, D. T. Burns, and P. Roger, "Determination of the specific heat capacity of a graphite sample using absolute and differential methods," Metrologia 44, 294-302 (2007).

Sander et al., "NPL's new absorbed dose standard for the calibration of HDR 192Ir brachytherapy sources," Metrologia 49, S184-S188 (2012).

Seuntjens et al., Review of Calorimeter Based Absorbed Dose to Water Standards, Standards and Codes of Practice in Medical Radiation Dosimetry, IAEA-CN-96-3, 2002 p. 37-66.

Stewart in "The Development of New Devices for Accurate Radiation Dose Measurement: A garded Liquid Ionization Chamber and an Electron Sealed Water Calorimeter" Ph. D. Dissertation McGill University, 2007.

Sundara et al., "Graphite Calorimeter in Water and Calibration of Ionization Chambers in Dose to Water for 60Co Gamma Radiation", Medical Physics, vol. 7, No. 3, May-Jun. 1980, pp. 196-201.

Witzani et al., "A Graphite Absorbed-Dose Calorimeter in the Quasi-Isothermal Mode of Operation", Metrologia, vol. 20, No. 3, 1984, pp. 73-79.

Y. Morishita et al., "A standard for absorbed dose rate to water in a 60Co field using a graphite calorimeter at the national metrology institute of Japan," Radiat. Prot. Dosim. 1-9 (2012) (published E-first Sep. 5, 2012).

Brusasco, C, et al. 'A Dosimetry System for Fast Measurement of 3D Depth-dose Profiles in Charged-particle Tumor Therapy with Scanning Techniques.' Nuclear Instruments & Methods In Physics Research, Section—B: Beam Interactions With Materials And Atom 168.4 (2000): 578-92.

PCT App. No. PCT/US2015/024360; International Search Report and Written Opinion mailed Oct. 8, 2015; 13 page.

(56) References Cited

OTHER PUBLICATIONS

PCT App. No. PCT/US2015/024360; International Preliminary Report on Patentability Chapter I mailed Oct. 4, 2016; 9 pages.
Nelms, Benjamin. "Variation in External Beam Treatment, Plan Quality: An Inter-institutional Study of Planners and Planning Systems." Practical Radiation Oncology 2.4 (2012): 296-305.
PCT App. No. PCT/US2014/065808; International Search Report and Written Opinion mailed May 21, 2015; 9 pages.
PCT App. No. PCT/US2014/065808; International Preliminary Report on Patentability Chapter I mailed May 17, 2016; 7 pages.
Mackie et al., "Photon Beam Dose Computations", Proceedings of the 1996 AAPM Summer School, 1996. 36 pages.
PCT App. No. PCT/US2012/058345; International Search Report mailed Apr. 17, 2013; 3 pages.
Ahnesjo et al., "Calculation and Application of Point Spread Functions for Treatment Planning with High Energy Photon Beams", Acta. Oncol., 26, 49-56, 1987.
PCT App. No. PCT/US2012/058345; International Preliminary Report on Patentability Chapter I mailed Apr. 1, 2014; 5 pages.
PCT App. No. PCT/US2012/058345; International Written Opinion of the International Search Authority mailed Mar. 29, 2014; 4 pages.
Ahnesjo et al., "Dose calculations for external photon beams in radiotherapy", Phys. Med. Biol. 44, R99-R155 1999.
Ahnesjo, "Collapsed Cone Convolution of Radiant Energy for Photon Dose Calculation in Heterogeneous Media", Med. Phys. 16, 577-92, 1989.
Amanatides et al., "A Fast Voxel Traversal Algorithm for Ray Tracing", Eurographics '87, Conference Proceedings, 1987, 10 pages.
PCT App. No. PCT/US2018/020320; International Preliminary Report on Patentability Chapter I mailed Sep. 12, 2019. pp. 1-11.
PCT Appl. No. PCT/US2018/056568; International Preliminary Report on Patentability, mailed Apr. 30, 2020. 8 pages.
International Search Report and Written Opinion mailed Oct. 2, 2020, PCT Application No. PCT/US2020/041458.
International Search Report and Written Opinion mailed Nov. 24, 2021, PCT Application No. PCT/IB2021/057573.
Liu et al., "Correcting kernel tilting and hardening in convolution/superposition dose calculations for clinical devergent and polychomatic photon beams", Med. Phys. 24, 1729-1741, 1997.
Lu et al., "Accurate convolution/superposition for multi-resolution dose calculation using cumulative tabulated kernels", Phys. Med. Biol. 50, 655-680, 2005.
Mackie et al., The Use of Comp. In Rad. Ther., 107-110 1987.
Mackie et al., "Generation of Photon Energy Deposition Kernels Using the EGS Monte Carlo Code," 1988, Phys. Med. Biol. 33, pp. 1-20.
Mackie et al., "A convolution method of calculating dose for 15-MVx rays", Med. Phys. 12, 188-196, 1985.
Mohan et al., "Energy and angular distributions of photons from medical linear accelerators", Med. Phys. 12, 592-597, 1985.
Otto, "Volumetric modulated arc therapy: IMRT in a single gantry arc", Med. Phys. 35, 310-317, 2008.
Papanikolaou et al., "Investigation of the convolution method for polyenergetic spectra", Med. Phys. 20, 1327-1336, 1993.
Williams, "Pyramidal Parametrics", SIGGRAPH Comput. Graph. 17, 3, 1-11, 1983.
Yan et al., "Adaptive radiation therapy", Phys. Med. Biol. 42, 123-132, 1997.
Yu, "Intensity-modulated arc therapy with dynamic multileaf collimation: an alternative to tomotherapy", Phys. Med. Biol. 40, 1435-1449, 1995.
PCT App. No. PCT/US2009/043341; International Search Report mailed Jan. 5, 2010. 3 pages.
PCT App. No. PCT/US2009/043341; Written Opinion of the International Search Authority mailed Nov. 8, 2010. 3 pages.
PCT App. No. PCT/US2009/043341; International Preliminary Report on Patentability Chapter I mailed Nov. 9, 2010. 4 pages.
PCT App. No. PCT/US2012/053440; International Search Report and Written Opinion mailed Mar. 26, 2014; 3 pages.

"Waterphantom Dosimetry"; Medical Physics, vol. 3, May/Jun. 1976; pp. 189.
Indra J. Das, Chee-Wai Cheng, Ronald J. Watt, Anders Ahnesjo, John Gibbons, X. Allen Li, Jessica Lowenstien, Raj K. Mitra, William E. Simon, Timothy C. Zhu; Accelerator Beam Data Commissioning Equiptment and Procedures; Report of the TG-106 of the Therapy Physics Committee of the AAPM; Med. Phys. 35(9), Sep. 2008; pp. 4186-4215.
PCT App. No. PCT/US2010/042680; International Search Report mailed Jan. 27, 2011; 2 pages.
PCT App. No. PCT/US2010/042680; International Written Opinion mailed Jan. 23, 2012; 8 pages.
PCT App. No. PCT/US2010/042680; International Preliminary Report on Patentability Chapter I mailed Jan. 24, 2012; 9 pages.
EP2457237 Supplemental European Search Report and Written Opinion mailed Mar. 8, 2017; 10 pages.
PCT App. No. PCT/US2009/036775; International Search Report mailed Nov. 12, 2009; 2 pages.
PCT App. No. PCT/US2009/036775; International Preliminary Report on Patentability Chapter II and Written Opinion mailed Sep. 12, 2010; 12 pages.
EP2277353 Search Report mailed Jul. 21, 2017; 10 pages.
Benedick Fraass; "Quality Assurance for Clinical Radiotherapy Treatment Planning," Med Phys., 25(10), Oct. 1998; pp. 1773-1829.
G.J. Kutcher; "Comprehensive AQ for Radiation Oncology Report;" AAPM Radiation Therapy Committee Task Group 40; Med. Phys., 21; Apr. 1994; pp. 581-618.
MapCheck and EPIDose; www.sunnuclear.com; manufactured by Sun Nuclear Corp.; Melbourne,FL; 2010, 8 pages.
MapCALC; www.sunnuclear.com; manufactured by Sun Nuclear Corp.; Melbourne, FL; 2009, 2 pages.
Joseph O. Deasy; "A Computational Environment for Radiotherapy Research," Med. Phys. 30, (5), May 2003; pp. 979-985.
Robert M. Eisberg; "Fundamentals of Modern Physics," Chapter 9—Perturbation Theory; John Wiley & Sons; 1967; pp. 268-272.
Cyberknife; Cyberknife Systems; "The Standard of Radiosurgery", by Accuracy, Sunnyvale, CA; 2009; pp. 1-6.
"HI-ART"; www.tomotherapy.com; TomoTherapy, Madison, WI; 2007; pp. 1-8.
"Rapid Arc"; Varian Medical Systems, Inc., Palo Alto, CA; www.varian.com; 2007; pp. 1-8.
"VMAT"; Elekta, Ltd., Crawley UK; Document No. 4513 3710770; Oct. 8, 2008, 8 pages.
D.W.O. Rogers; "Montey Carlo Techniques in Radiotherapy," Physics in Canada, Medical Physics Special Issue, v. 58 #2; 2002; pp. 63-70.
T.R. McNutt, T.R. Mackie, P.J. Reckwerdt, B.R. Paliwal; "Analysis and Convergence of the Iterative Convolution/Superposition Dose Reconstruction Technique,"; Med. Phys. 24(9) Sep. 1997; pp. 1465-1476.
Mathilda Van Zijtveld, Maaretn L.P. Dirkxa, Hans C.J. De Boera, and Ben J.M. Heijmen; "3D Dose Reconstruction for Clinical Evaluation of IMRT Pretreatment Verification with an EPID." Radiotherapy and Oncology, 32(2); Feb. 2007; pp. 201-201.
PCT App. No. PCT/US2009/036917; International Search Report mailed Sep. 17, 2009. 2 pages.
PCT App. No. PCT/US2009/036917; Written Opinion mailed Sep. 12, 2010; 4 pages.
PCT App. No. PCT/US2009/036917; International Preliminary Report on Chapter II Patentability mailed Mar. 15, 2011. 3 pages.
PCT/US2017/044472; International Search Report and Written Opinion of the International Searching Authority, or the Declaration mailed Oct. 13, 2017; 12 pages.
PCT App. No. PCT/US2012/053440; International Preliminary Report on Patentability Chapter I mailed Mar. 3, 2015; 8 pages.
PCT App. No. PCT/US2016/028664; International Preliminary Report on Patentability mailed Nov. 2, 2017; 5 pages.
PCT App. No. PCT/US2017/062608; International Search Report and Written Opinion mailed Feb. 22, 2018; 11 pages.
McEwen et al.; "A portable calorimeter for measuring absorbed dose in radiotherapy clinic"; Dec. 2000; Phys. Med. Biol., vol. 45; pp. 3675-3691.

(56) References Cited

OTHER PUBLICATIONS

McDermott et al.; "Replacing Pretreatment Verification with In Vivo EPID Dosimetry for Prostate IMRT"; International Journal of Radiation: Oncology Biology Physics, Pergamon Press, USA, vol. 67, No. 5, Mar. 28, 2007, pp. 1568-1577, XP022101268, ISSN: 0360-3016, DOI: 10.1016/J.IJROBP.2006.11.047.

Nelms, Benjamin et al.; "Evalution of a Fast Method of EPID-based Dosimetry for Intensity-modulated Radiation Therapy"; Journal of Applied Clinical Medical Physics, Jan. 1, 2010, pp. 140-157, XP055476020.

PCT App. No. PCT/US2018/020320; International Search Report and Written Opinion mailed Jul. 24, 2018; 18 pages.

Linacre, J.K. , "Harwell Graphite Calorimeter", IAEA, vol. 47, 1970 (pp. 46-54.).

International Search Report and Written Opinion mailed Sep. 1, 2023, PCT Application No. PCT/iB/2023/055991.

* cited by examiner

HIGH DOSE RATE RADIATION THERAPY SYSTEMS AND DOSIMETRY

DESCRIPTION OF THE RELATED ART

Radiation therapy can be utilized in the treatment of diseases, for example, by delivering a dose of radiation to kill or to inhibit growth of a cancerous tumor. Devices to deliver radiation therapy can include, for example, radioisotopes, heavy ion accelerators and linear accelerators that generate a photon or electron beam directed at a tumor site. To irradiate a tumor while minimizing exposure to nearby healthy tissues, a radiation beam can be shaped by a collimating device, for example, a multileaf collimator (MLC).

Radiation therapy quality assurance can be performed to verify the proper operation of one or more components of a radiation therapy delivery system, for example, verifying the amount of radiation provided by a radiation source. Devices used with such radiation therapy quality assurance can include radiation detectors such as ion chambers or radiation sensitive diodes.

SUMMARY

Disclosed herein is a system for quality assurance of high dose rate radiation therapy. The system includes a radiation delivery system configured to deliver high dose rate radiation therapy, with the radiation delivery system including a radiation source and a collimating system. The system also includes a radiation detection system having a diode to measure high dose rate radiation from the radiation source, an operational amplifier to transform the output of the diode to a measurable voltage, and a voltage source configured to apply a reverse bias to a component of the radiation detection system.

In an interrelated aspect, also disclosed is a system for quality assurance of high dose rate radiation therapy. In this interrelated aspect, the system includes a radiation detection system having a diode to measure high dose rate radiation from a radiation source, an operational amplifier to transform the output of the diode to a measurable voltage, and a voltage source configured to apply a reverse bias to a component of the radiation detection system.

In some variations, the radiation delivery system can be configured to deliver an instantaneous dose rate in the range of $2 \times 10^4$ Gy/s to $1 \times 10^7$ Gy/s.

In other variations, the reverse bias can reduce a loss of sensitivity of the radiation detection system when measuring the high dose rate radiation. The reverse bias can keep the loss of sensitivity of the radiation detection system to no more than 2%.

In yet other variations, the high dose rate radiation can create a forward bias that reduces the sensitivity of the radiation detection system and the voltage source can apply a reverse bias that removes at least 95% of the forward bias. The voltage source can be applied to a noninverting input of the amplifier. The voltage source can produce a voltage bias across inputs of the amplifier that is maintained by the output of the amplifier via a feedback capacitor.

In some variations, a capacitor can be connected in parallel to the diode, thereby reducing a forward bias of the diode. The radiation detection system can also include an input resistor between the diode and the operational amplifier.

In other variations, the voltage source can be configured to apply up to 10.0 V to form the reverse bias.

In an interrelated aspect, a system for quality assurance of high dose rate radiation therapy delivery from a radiation source is disclosed. The system includes a diode to measure high dose rate radiation from the radiation source and a radiation detection system including an amplifier to transform the output of the diode to a measurable voltage. The amplifier is configured to have an inherent bias that effectively reverse biases the radiation detection system.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Figure 1A:
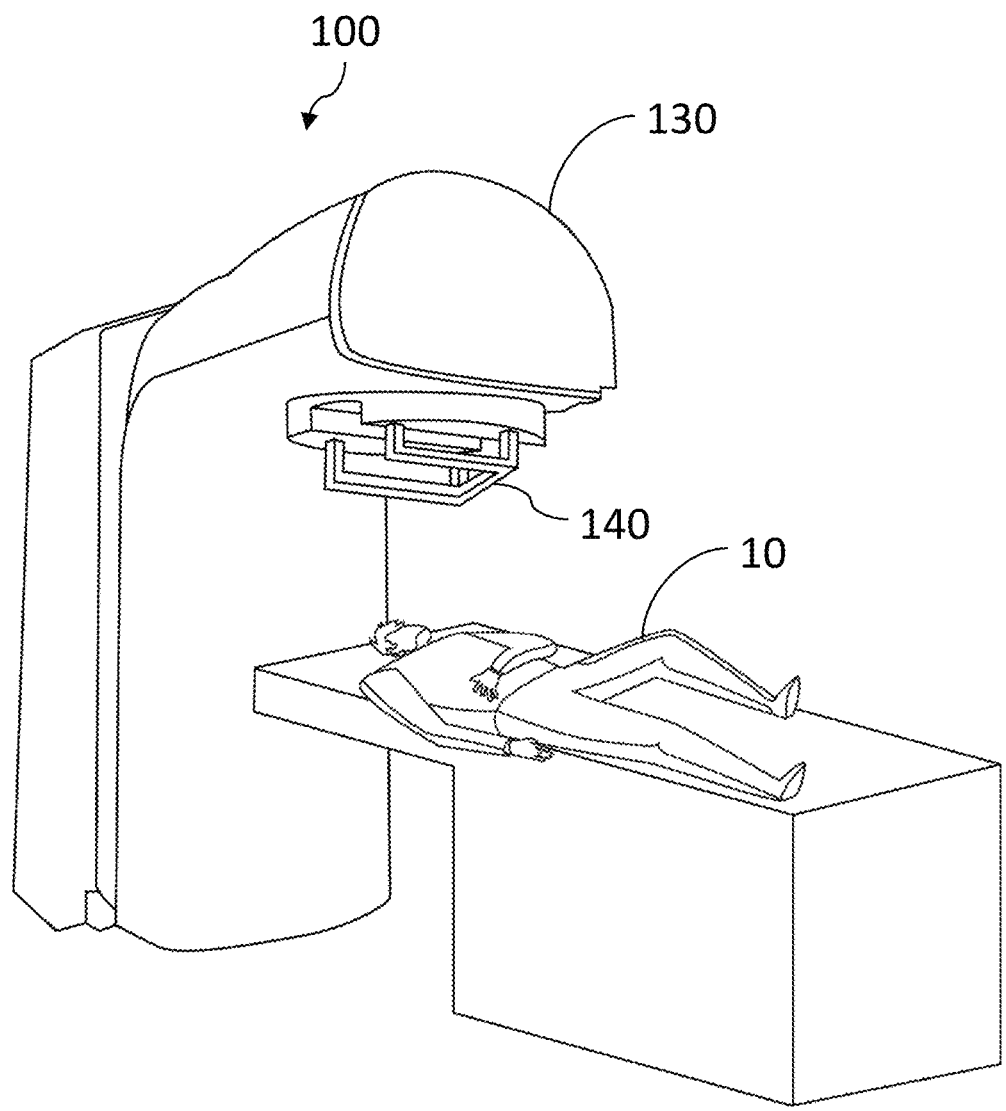
FIG. 1A is a diagram illustrating a perspective view of a simplified exemplary radiation delivery system configured to deliver high dose rate radiation therapy in accordance with certain aspects of the present disclosure.
Figure 1B:
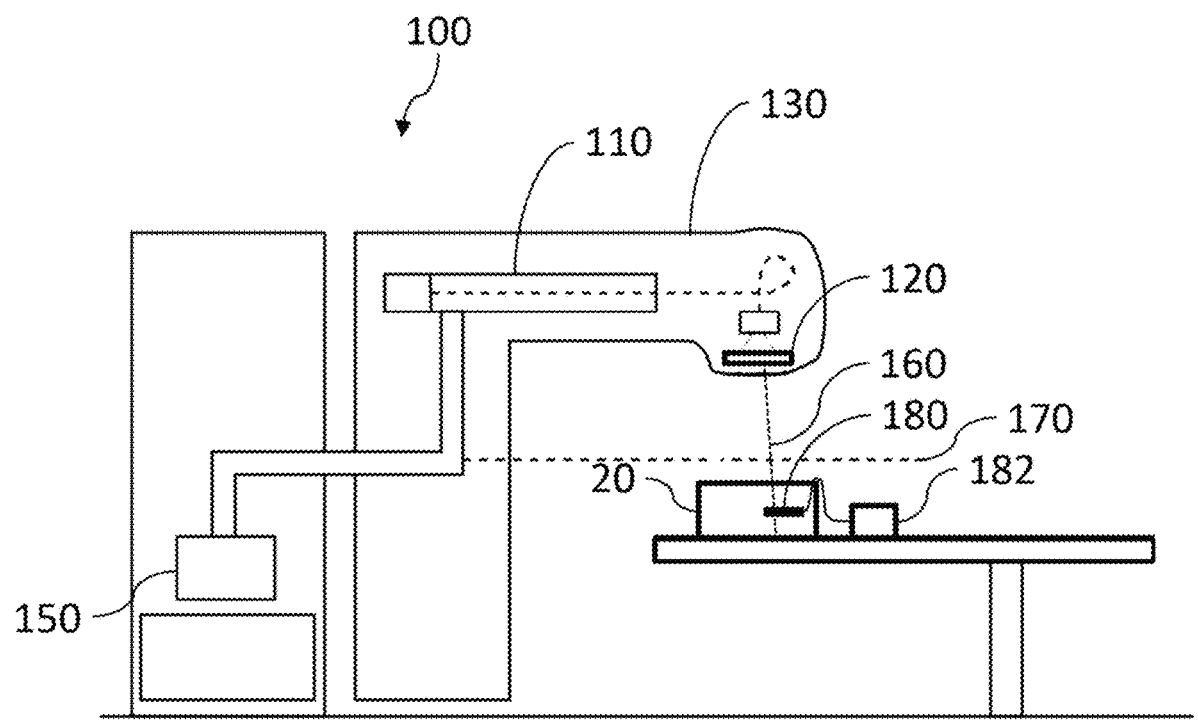
FIG. 1B is a diagram illustrating a side-sectional view of the simplified exemplary radiation delivery system of FIG. 1A in accordance with certain aspects of the present disclosure.

FIGS. 1A and 1B depict an exemplary radiation delivery system 100 configured to deliver high dose rate radiation therapy. The radiation delivery system can include a radiation source and a collimating system. The system shown is an open (or "C-arm") type system that includes a radiation source such as a linear accelerator (e.g., element 110 in FIG. 1B) working with an RF source 150, a collimating system such as a multileaf collimator 120, and a rotatable gantry 130. In this exemplary system, the linear accelerator and multileaf collimator are mounted within the rotatable gantry to allow radiation beam 160 to be delivered to a patient 10 at multiple angles (e.g., about rotation axis 170). FIG. 1A also depicts an accessory tray 140 that can permit the mounting or positioning of hardware or devices between the radiation source and the patient. As described further herein, the technologies of the present disclosure can be used with radiation delivery systems such as the exemplary system depicted in FIGS. 1A and 1B, as well as with other types of radiotherapy systems such those utilizing ring-gantries, robotic arms, etc.

FIG. 1B also depicts an exemplary radiation detection system for performing quality assurance of the radiation delivery system. In the example of FIG. 1B, the radiation detection system can include a radiation detector 180 and detector electronics 182. In some embodiments, the radiation detection system can be utilized with a phantom 20. In various embodiments, the phantom can be, for example, a water phantom, a solid phantom, etc.

Radiation detector 180 can be for example, a diode-based radiation detector, an ionization chamber, etc. In some embodiments described below, the radiation detector is a diode that may be utilized with or without a phantom. To facilitate acquisition and analysis of radiation detected at the detector, detector electronics 182 can be included that may include amplifiers, voltage sources, analog-to-digital-converters, digitizers, etc.

Figure 2:
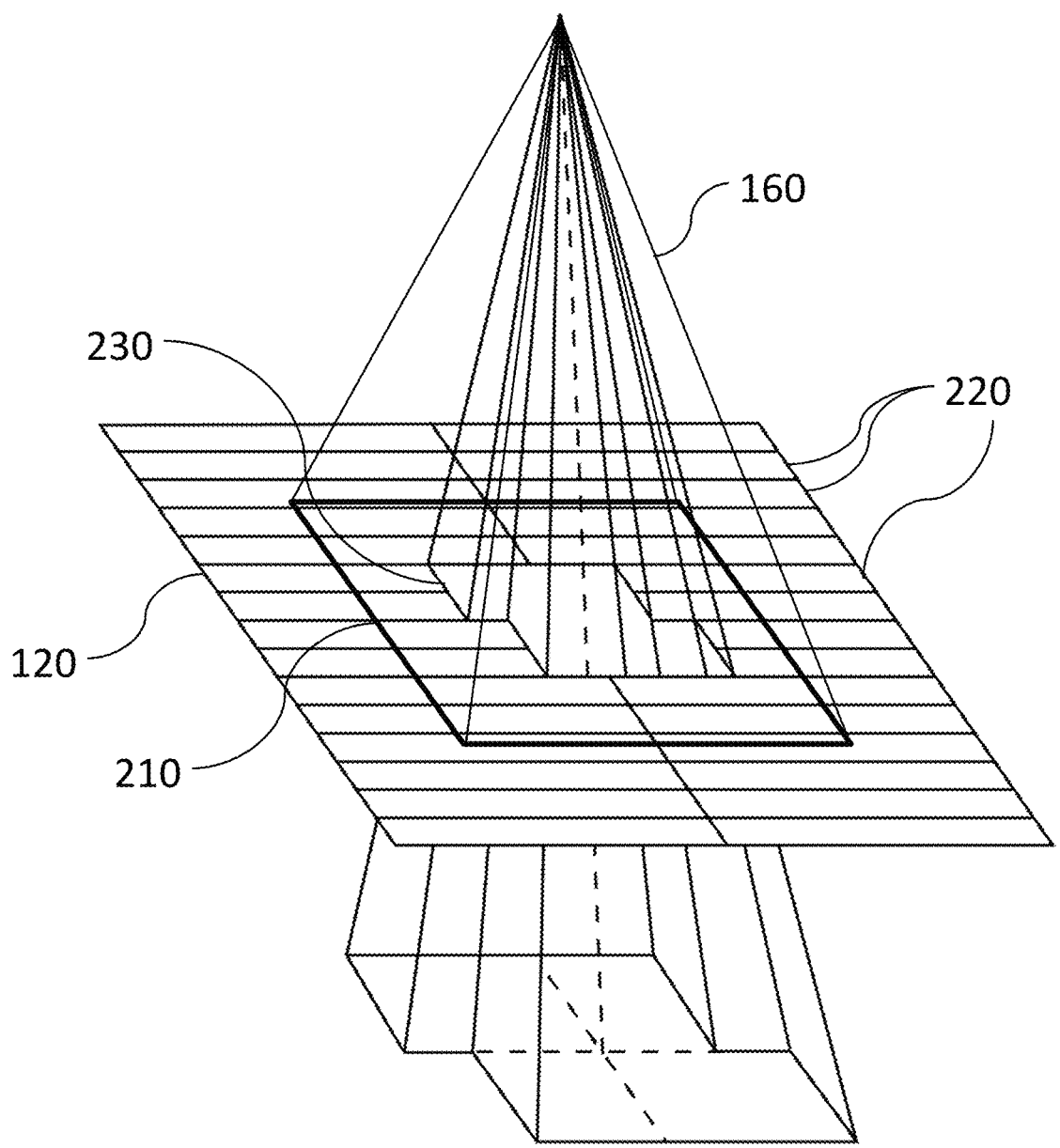
FIG. 2 is a diagram illustrating a perspective view of a simplified exemplary multileaf collimator shaping a radiation field in accordance with certain aspects of the present disclosure.

FIG. 2 is a diagram illustrating a perspective view of a simplified exemplary multileaf collimator shaping a radiation field. When performing radiation therapy quality assurance with the radiation detector, one element of the radiation therapy device that can be assessed is the operation of the multileaf collimator (MLC) (e.g., through verifying the collimator's leaf positions). One method for MLC configuration verification may involve examining the shape of the radiation field delivered to the patient. As shown in the simplified example of FIG. 2, a radiation field 210 can be shaped by blocking some portions with the leaves 220 of the multileaf collimator 120 to form an aperture 230. The portion of the radiation field that passes through the aperture will then proceed to the patient to deliver a dose of radiation in the desired shape. In other embodiments, apertures can be formed with fixed openings such as cutouts in shielding or cones with holes to allow radiation to pass through. As used herein, the term "radiation field" can refer to radiation before or after being shaped by a collimator.

In some embodiments, diode-based radiation detectors can have benefits for use in quality assurance due to their small size facilitating their ability to measure radiation fields with a high spatial resolution. Such diodes can be particularly useful in measuring the edges of a radiation field where the radiation dose gradient may be quite large. Additionally, high-resolution measurements can be beneficial for small radiation patterns such as those utilized for stereotactic radiosurgery (SRS).

One method of radiation treatment addressed herein is described as "high dose rate radiation therapy." An example of such is sometimes referred to UH-DPP (ultra-high dose per pulse), where the instantaneous dose rate is many times higher than "conventional" radiation therapy. One example of instantaneous dose rates that may be delivered can be between $2 \times 10^4$ Gy/s and $1 \times 10^7$ Gy/s or even more. Such instantaneous dose rates can be delivered in one or more radiation pulses which may be repeated at rates of tens or hundreds of times per second. Some clinical studies have shown that such therapies (sometimes referred to as FLASH radiation therapy) can have improved patient outcomes by reducing healthy tissue damage while maintaining therapeutic effect to tumor. As used herein, "high dose rate radiation/ radiation therapy" means delivering radiation at an instantaneous dose rate of at least $1 \times 10^4$ Gy/s.

Figure 3:
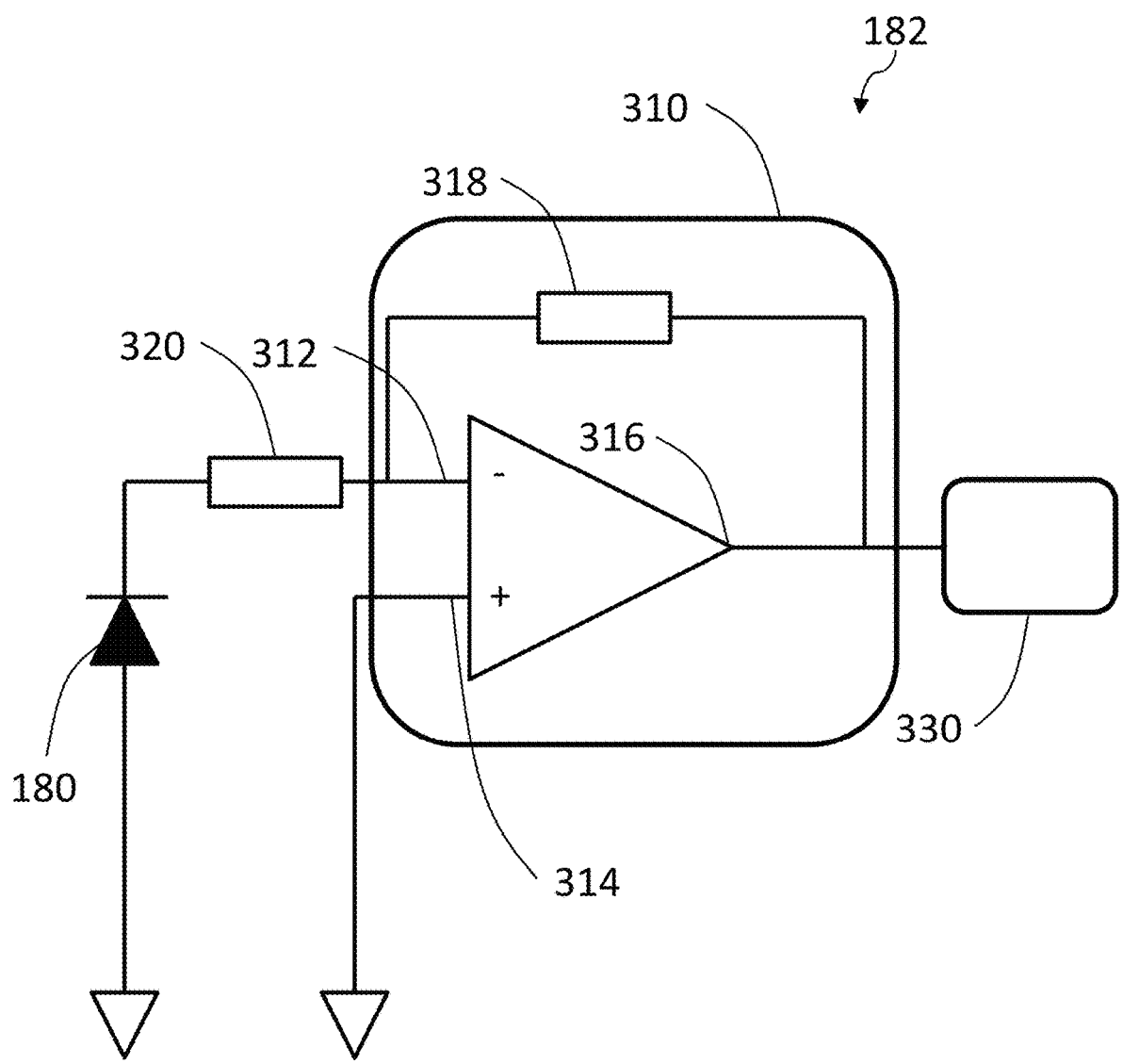
FIG. 3 is a diagram illustrating a simplified diagram of a portion of a radiation detection system in accordance with certain aspects of the present disclosure.

FIG. 3 is a diagram illustrating a simplified example of a radiation detection system, or a portion thereof, that can be used for measuring radiation dose. As depicted in FIG. 3, the radiation detection system can include a radiation detector 180 (also referred to herein as diode 180) to measure dose from the radiation source. Diode 180 can be a solid-state diode that is sensitive to incoming radiation. For example, such a diode includes a depletion zone between "P" and "N" (pn) regions of the diode. The depletion zone is an intrinsic region at the pn boundary, formed by thermal diffusion of holes from the p side to the n region and electrons from the n side to the p region until equilibrium is reached, resulting in an electric field, i.e., voltage potential across the pn junction. The intrinsic region is devoid of free charge carriers, referred to as a depletion zone. Any free charge carriers injected into the intrinsic region are swept away by the electric field in order to maintain equilibrium. When the diode is irradiated, ion pairs (holes and electrons) are produced in proportion to the radiation dose delivered. The ion pairs thermally diffuse until they are either trapped within their region of origin or, if they enter the depletion zone, are conducted by the electric field to the other region, thereby forming a measurable charge that can be related to the radiation dose. The lifetime of the diffusion process before trapping is reasonably long, on the order of 1 microsecond, depending on various conditions of the diode substrate such as lattice defects, resistivity, impurity doping, etc.

As shown in the example of FIG. 3, the charge (or 'signal') out of the diode can go to an amplifier with other side of the diode connected to ground. The orientation (i.e., polarity) of the diode determines the signal polarity to the electrometer, which determines the output polarity of the amplifier. It also determines the effect that an amplifier input offset voltage has on the diode junction voltage which affects the charge collected from the irradiated diode. Either orientation of the diode can be utilized for radiation detection as long as the amplifier power supply has the correct polarity to service the feedback for the diode charge. If the diode polarity is flipped, then the input offset voltage must also 'flip' to keep the diode reversed biased.

In some embodiments, amplifier 310 can be included to transform the output of the diode to a measurable voltage. While the present disclosure contemplates that any type of amplifier can be utilized, the detailed embodiments provided herein are expressed as utilizing an operational amplifier (or "op-amp"). The amplifier can include an inverting input 312, a noninverting input 314, and an output 316. The inverting input is depicted as receiving charge from the diode, whereas the noninverting input is connected to ground. In some embodiments, the amplifier can include a feedback capacitor 318 that can be connected across the amplifier. In the example shown, the feedback capacitor is connected across the inverting input 312 and the output 316. The output of the amplifier may then be directed to measurement electronics 330, which can include any combination of, for example, an electrometer/voltmeter, other amplifiers, a digitizer, a display device, etc.

To prevent oscillations due to internal or intentional parallel capacitance of the diode, some embodiments can optionally include an input resistor 320 between the diode and the operational amplifier.

It is emphasized here that while the present disclosure contemplates the use of the radiation detection system with a radiation delivery system, that any purported "invention" does not require the inclusion of the radiation delivery system. In other words, the radiation detection system (e.g., any combination of diodes, amplifiers, voltage sources, etc.) can be a standalone system—apart from radiation therapy systems/sources that provide the radiation that the radiation detection system measures.

Figure 4:
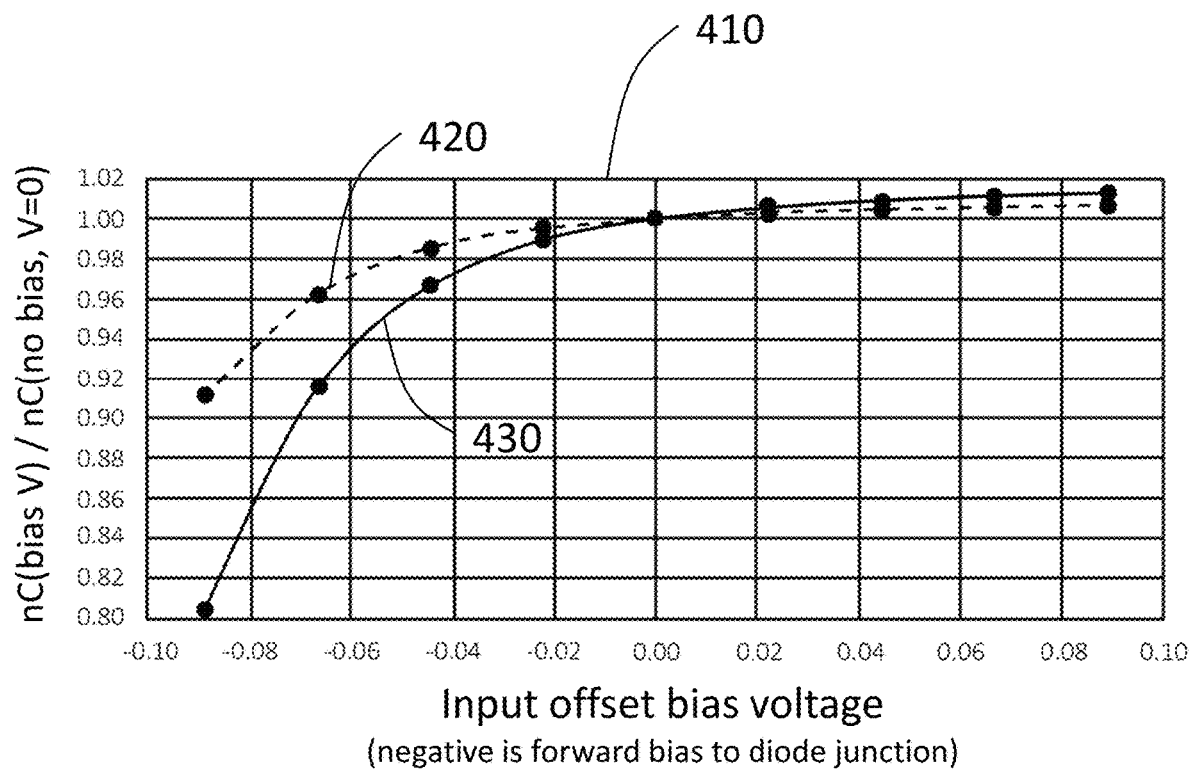
FIG. 4 is an exemplary plot of measurement sensitivity ratios in a diode as a function of input offset bias voltage in accordance with certain aspects of the present disclosure.

FIG. 4 is an exemplary plot of measurement sensitivity ratios in a diode as a function of bias voltage. The X-axis of FIG. 4 represents an exemplary input offset bias voltage (when the voltage is negative, it is considered to be a forward bias to the diode when the diode connection to the inverting input causes the amplifier output to go positive). The Y-axis represents a ratio of sensitivities, specifically, the sensitivity (e.g., nanocoulombs per gray) observed with a particular offset bias voltage, divided by the sensitivity that would be observed if the offset bias voltage was zero.

The plot 410 of FIG. 4 shows one example of how a diode can lose measurement sensitivity for some values of input offset bias voltage. The two curves depicted in plot 410 are for diodes that are leak corrected (i.e., dashed curve 420) and diodes that are not leak corrected (i.e., solid curve 430). While diodes may include leak correction (e.g., to adjust for diode "dark" currents resulting from non-radiation effects), FIG. 4 shows that the general dependence of sensitivity ratio versus input offset bias voltage remains nearly constant while the diode junction is reverse biased. It is instructive to note that, as shown by FIG. 4, diode sensitivity can be highly dependent on offset bias voltage, particularly when there is a forward bias to the diode junction.

The incidence of radiation dose to the diode, combined with resistance in the path between the diode and the amplifier input, can create a voltage drop across the resistance that can forward bias the diode junction with the effect of reducing the junction voltage of the diode. This can effectively create a new equilibrium state of the diode junction as originally formed in the absence of the diode's response to radiation. The reduction of the junction voltage will then diminish the diode signal, as seen in FIG. 4. As the instantaneous dose rate increases, the number of the ion pairs formed in the diode can also increase. This can increase the voltage drop across the input resistor 320 which further reduces the diode output, having the effect of limiting the forward bias increase until the diode loses the ability to collect the diffused ion pairs, reaching an equilibrium of a portion of the ion pairs constituting a signal. The resistance that causes the voltage drop between the diode and the amplifier can be caused by, for example, actual resistors in the circuit (e.g., input resistor 320), resistance of the conductor(s) (i.e., resistance in the wiring connecting the diode to the amplifier), etc. The present disclosure provides numerous embodiments that address this and other technical problems.

The application of a "reverse bias" in this context is discussed below. Because sign conventions for diodes and amplifiers can vary—as used herein, a negative input offset bias voltage shown in FIG. 4 is referred to as a "forward biasing" of the diode. Accordingly, various embodiments of the present disclosure can include a voltage source configured to apply a "reverse bias" to a component of the radiation detection system that acts to reduce the forward bias, thus reducing a loss of sensitivity of the radiation detection system when measuring high dose rate radiation. As used herein, applying a reverse bias does not mean changing the direction of current flow through the diode, but instead refers to the application of a voltage that maintains the diode junction voltage at its nominal value thereby maintaining the diode signal response to dose.

For detectors utilized in radiation therapy quality-assurance, measurement sensitivity must be maintained in order to accurately measure radiation dose output of a delivery system. This can be a challenge with conventional measurement methods when the radiation delivery system is configured to deliver high instantaneous dose rates (in one particular example, from $2\times10^4$ Gy/s through $1\times10^7$ Gy/s). The improved radiation detection systems of the present disclosure can thus include the application of a reverse bias to a component of the radiation detection system that will keep the loss of sensitivity of the radiation detection system to no more than 2%.

When the present disclosure refers to a loss of sensitivity, such is intended to reflect the concept depicted in the example of FIG. 4 (e.g., a sensitivity loss of 2% would equate to a level of 0.98 on the vertical axis). As shown in FIG. 4, sensitivity loss can be minimized by reducing the forward bias by a requisite amount (e.g., reducing a 0.09V forward bias by approximately 50% to 0.05V can result in the loss of sensitivity being no more than 2%. As another example, reducing a 0.06V forward bias by approximately 30% to 0.02V can result in the loss of sensitivity being no more than 0.5%.

In addition, the system can be configured such that the sensitivity loss can be, for example, no more than 1%, 3% or 5%. The desired sensitivity can be application dependent and thereby vary based on the needs of the user and the particular hardware involved. Thus, the present disclosure contemplates that the forward bias can be changed or compensated for by any of the methods disclosed herein as needed to provide the desired sensitivity of the radiation detection system.

In various embodiments described herein, the radiation detection system can include a voltage source configured to apply reverse bias to a component of the radiation detection system. Examples of voltage sources can include power supplies, batteries, capacitors, etc.

Figure 5:
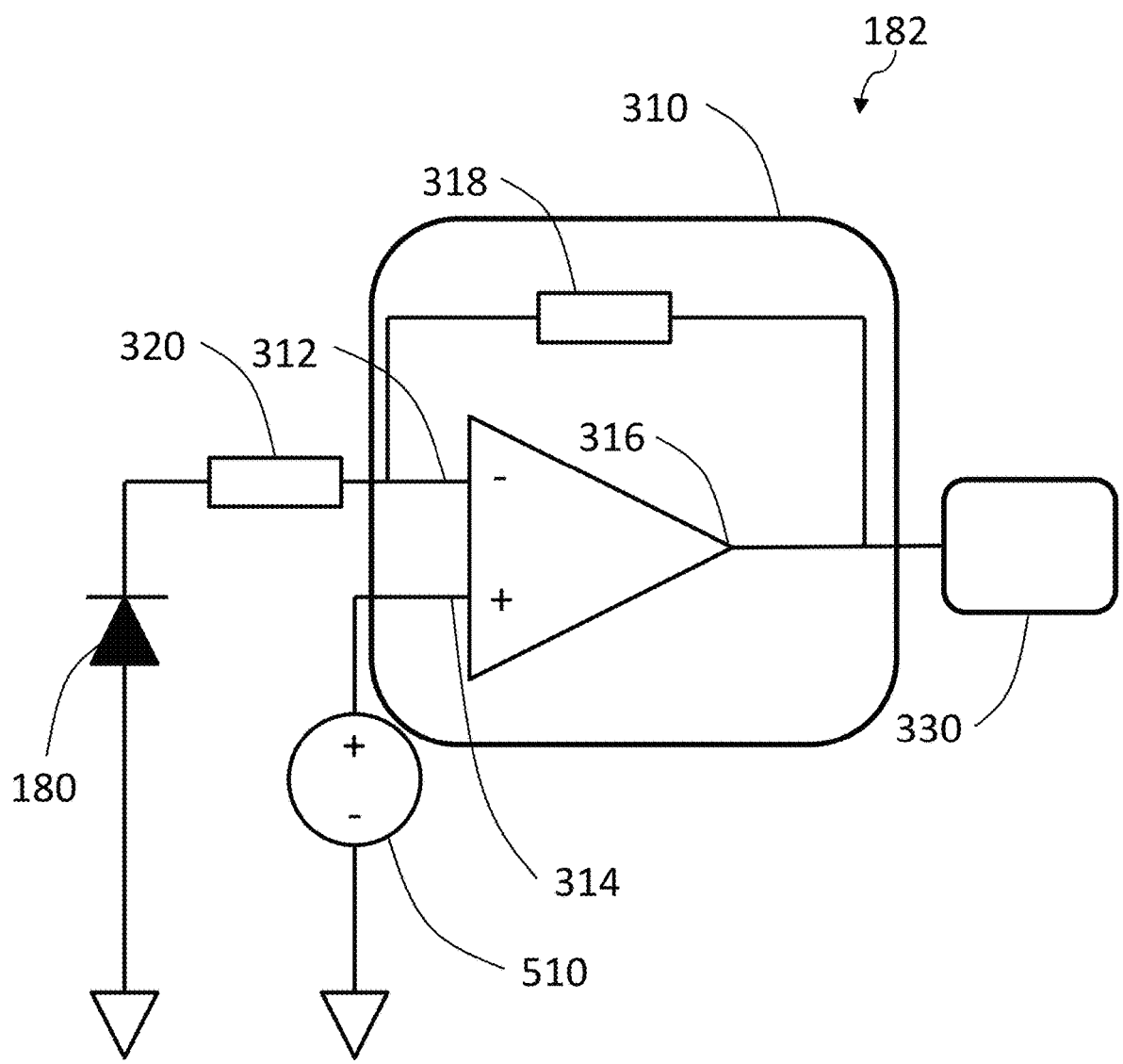
FIG. 5 is a diagram illustrating a simplified example of a voltage source connected to an amplifier to apply a reverse bias to the diode in accordance with certain aspects of the present disclosure.

FIG. 5 is a diagram illustrating a simplified example of a voltage source connected to an amplifier to provide the application of a reverse bias. In the embodiment of FIG. 5, the voltage source 510 can be applied to the amplifier noninverting input 314 and can produce a voltage bias across the inputs of the amplifier which is maintained by the output of the amplifier via the feedback capacitor 318. This can have the effect of maintaining the diode junction voltage for the charge collection of ion pairs during irradiation. Accordingly, the input offset voltage can be controlled such that the loss of sensitivity is mitigated for the desired application.

In various embodiments, either orientation of the diode can be utilized for radiation detection as long as the voltage source 510 is bipolar, or at arranged with the correct polarity to provide the feedback for the diode current. For example, if the diode polarity in FIG. 5 is flipped, then the voltage source 510 must also 'flip' to keep the diode reversed biased. Accordingly, the meaning of reverse bias is understood to be defined with respect to current flow in the diode and not based on any particular configuration shown by the exemplary figures and symbols provided herein.

Figure 6:
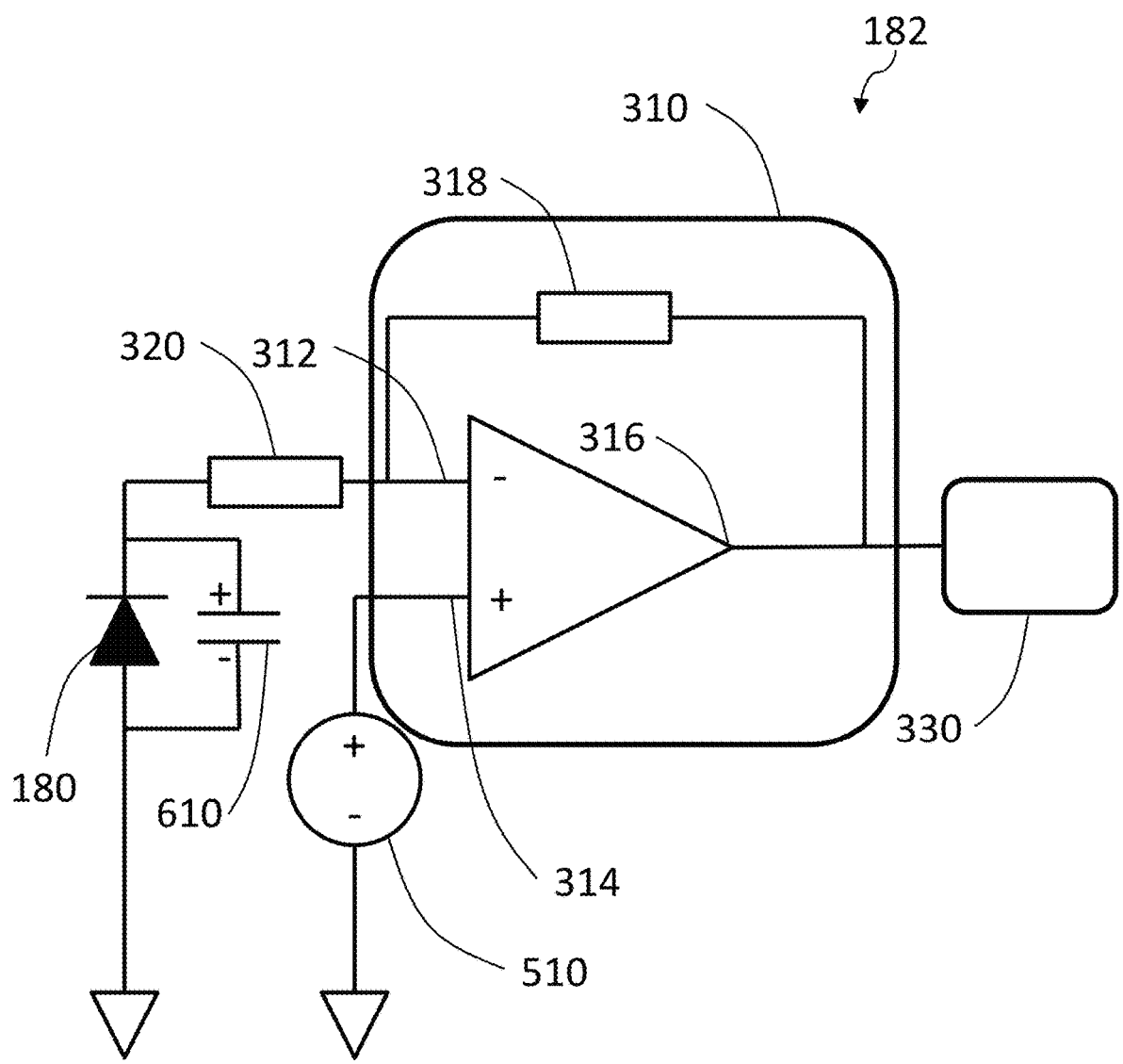
FIG. 6 is a diagram illustrating a simplified example of a capacitor connected in parallel to the diode in accordance with certain aspects of the present disclosure.

FIG. 6 is a diagram illustrating a simplified example of a capacitor connected in parallel to the diode. In the embodiment of FIG. 6, a capacitor 610 (also referred as a buffer capacitor) is connected in parallel to the diode, thereby reducing a forward bias of the diode. The buffer capacitor can accumulate charge from the diode, which reduces the forward bias since voltage is inversely proportional to capacitance value. FIG. 6 also illustrates the implementation of a bias (e.g., via voltage source 510) between the noninverting (+) input 314 and ground. The buffer capacitor 610 can mitigate the voltage across the junction which is related to the junction capacitance. Adding the buffer capacitor 610 in parallel can reduce that voltage caused by charge from the diode.

While the buffer capacitor 610 in FIG. 6 may also forward bias the diode 180 as charge accumulates, buffer capacitor 610 can store charge from diode 180 during a radiation pulse, giving the charge time to transfer to the amplifier. The reverse bias supply (e.g., from voltage source 510) on the noninverting input 314 of the amplifier can mitigate the forward bias from the buffer capacitor.

As seen from the disclosed embodiments, the present disclosure describes numerous ways to apply a reverse bias to maintain the sensitivity of the radiation detection system when measuring high dose rate radiation. Thus, while some embodiments have been described and depicted in the drawings in detail, other such variations are considered within the scope of the present disclosure.

In another embodiment, rather than (or in addition to) a reverse bias being applied by various voltage sources, certain amplifiers can be configured to have an inherent bias that effectively reverse biases the radiation detection system. In some embodiments, including but not limited to MOSFET amplifiers, the input offset bias voltage can be sensitive to radiation dose. Some amplifiers can be pre-irradiated to achieve an input offset voltage that would provide the reverse bias. The polarity of the input offset bias voltage can determine the polarity connection of the diode to achieve the reverse bias. A supply voltage for the amplifier can also be corrected for such operation. Such amplifiers can thus apply a reverse bias to the diode but without requiring a separate voltage source. Although, in some embodiments, a voltage source can be utilized in combination with such inherently biased amplifiers.

In the following, further features, characteristics, and exemplary technical solutions of the present disclosure will be described in terms of items that may be optionally claimed in any combination:

Item 1: A system for quality assurance of high dose rate radiation therapy, the system comprising: a radiation delivery system configured to deliver high dose rate radiation therapy, the radiation delivery system including a radiation source and a collimating system; and a radiation detection system comprising: a diode to measure high dose rate radiation from the radiation source; an operational amplifier to transform the output of the diode to a measurable voltage; and a voltage source configured to apply a reverse bias to a component of the radiation detection system.

Item 2: A system for quality assurance of high dose rate radiation therapy, the system comprising: a radiation detection system comprising: a diode to measure high dose rate radiation from a radiation source; an operational amplifier to transform the output of the diode to a measurable voltage; and a voltage source configured to apply a reverse bias to a component of the radiation detection system.

Item 3: A system as in any of the preceding items, wherein the radiation delivery system is configured to deliver an instantaneous dose rate in the range of $2 \times 10^4$ Gy/s to $1 \times 10^7$ Gy/s.

Item 4: A system as in any of the preceding items, wherein the reverse bias reduces a loss of sensitivity of the radiation detection system when measuring the high dose rate radiation.

Item 5: A system as in any of the preceding items, wherein the reverse bias keeps the loss of sensitivity of the radiation detection system to no more than 2%.

Item 6: A system as in any of the preceding items, wherein the high dose rate radiation creates a forward bias that reduces the sensitivity of the radiation detection system and the voltage source applies a reverse bias that removes at least 95% of the forward bias.

Item 7: A system as in any of the preceding items, wherein the voltage source is applied to a noninverting input of the amplifier.

Item 8: A system as in any of the preceding items, wherein the voltage source produces a voltage bias across inputs of the amplifier that is maintained by the output of the amplifier via a feedback capacitor.

Item 9: A system as in any of the preceding items, further comprising a capacitor connected in parallel to the diode, thereby reducing a forward bias of the diode.

Item 10: A system as in any of the preceding items, wherein the radiation detection system further comprises an input resistor between the diode and the operational amplifier.

Item 11: A system as in any of the preceding items, wherein the voltage source is configured to apply up to 10.0 V to form the reverse bias.

Item 12: A system for quality assurance of high dose rate radiation therapy delivery from a radiation source, the system comprising: a diode to measure high dose rate radiation from the radiation source; and a radiation detection system including an amplifier to transform the output of the diode to a measurable voltage, wherein the amplifier is configured to have an inherent bias that effectively reverse biases the radiation detection system.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A system for quality assurance of high dose rate radiation therapy, the system comprising:
    a radiation delivery system configured to deliver high dose rate radiation therapy, the radiation delivery system including a radiation source and a collimating system; and
    a radiation detection system comprising:
        a diode to measure high dose rate radiation from the radiation source;
        an operational amplifier to transform an output of the diode to a measurable voltage; and
        a voltage source configured to apply a reverse bias to a component of the radiation detection system.

2. The system of claim 1, wherein the radiation delivery system is configured to deliver an instantaneous dose rate in the range of $2\times10^4$ Gy/s to $1\times10^7$ Gy/s.

3. The system of claim 1, wherein the reverse bias reduces a loss of sensitivity of the radiation detection system when measuring the high dose rate radiation.

4. The system of claim 3, wherein the reverse bias keeps the loss of sensitivity of the radiation detection system to no more than 2%.

5. The system of claim 1, wherein the high dose rate radiation creates a forward bias that reduces the sensitivity of the radiation detection system and the voltage source applies the reverse bias to remove at least 95% of the forward bias.

6. The system of claim 1, wherein the voltage source is applied to a noninverting input of the amplifier.

7. The system of claim 6, wherein the voltage source produces a voltage bias across inputs of the amplifier that is maintained by an output of the amplifier via a feedback capacitor.

8. The system of claim 1, further comprising a capacitor connected in parallel to the diode, thereby reducing a forward bias of the diode.

9. The system of claim 1, wherein the radiation detection system further comprises an input resistor between the diode and the operational amplifier.

10. The system of claim 1, wherein the voltage source is configured to apply up to 10.0 V to form the reverse bias.

11. A system for quality assurance of high dose rate radiation therapy delivery from a radiation source, the system comprising:
 a diode to measure high dose rate radiation from the radiation source; and
 a radiation detection system including an amplifier to transform the output of the diode to a measurable voltage, wherein the amplifier is configured to have an inherent bias that effectively reverse biases the radiation detection system.

* * * * *